US005463088A

United States Patent [19]
Lui et al.

[11] Patent Number: 5,463,088
[45] Date of Patent: Oct. 31, 1995

[54] PROCESS FOR PREPARING PERFLUOROALKOXY (ALKYLTHIO) BENZENES

[75] Inventors: Norbert Lui, Cologne; Albrecht Marhold, Leverkusen; Karl-Rudolf Gassen, Ratingen, all of Germany

[73] Assignee: Bayer Aktiengesellschaft, Leverkusen, Germany

[21] Appl. No.: 233,488

[22] Filed: Apr. 26, 1994

[30] Foreign Application Priority Data

May 3, 1993 [DE] Germany .................. 43 14 498.5

[51] Int. Cl.[6] .................. C07D 319/20; C07D 317/46; C07C 43/205; C07C 321/30
[52] U.S. Cl. .................. 549/362; 549/32; 549/15; 568/56; 568/649; 568/655; 568/656
[58] Field of Search .................. 568/655, 56, 649, 568/656; 549/362, 32, 15

[56] References Cited

U.S. PATENT DOCUMENTS

| 4,436,942 | 3/1984 | Rader et al. | 570/145 |
| 4,620,040 | 10/1986 | Alsop | 568/656 |
| 4,727,187 | 2/1988 | Siegrist et al. | 564/89 |
| 5,047,584 | 9/1991 | Maul et al. | 562/852 |

FOREIGN PATENT DOCUMENTS 0100788  2/1984  European Pat. Off. .
0196529  10/1986  European Pat. Off. .

*Primary Examiner*—Nicky Chan
*Attorney, Agent, or Firm*—William C. Gerstenzang; Sprung Horn Kramer & Woods

[57] ABSTRACT

A process for preparing perfluoroalkoxy(alkylthio)benzenes from perfluorochloroalkoxy(alkylthio)-benzenes by reaction with hydrogen fluoride in the gas phase and in the presence of a catalyst.

8 Claims, No Drawings

PROCESS FOR PREPARING PERFLUOROALKOXY (ALKYLTHIO) BENZENES

The present invention relates to a particularly advantageous process for preparing perfluoroalkoxy(alkylthio)benzenes from perfluorochloroalkoxy(alkylthio)benzenes.

It is known that p-α, α-dichloro-β, β, β-trifluoroethoxy-benzotrichloride or -benzoyl chloride can be converted by hydrogen fluoride in the presence of a catalyst into p-pentafluoroethoxy-benzotrifluoride or -benzoyl fluoride (U.S. Pat. No. 5,047,584). In this method the catalysts used are, for example, antimony pentahalides and the reaction is carried out in the liquid phase at atmospheric or superatmospheric pressure. The yields are between 51 and 69%.

It is also known that α, α-difluorophenyl ether can be prepared by fluorinating the corresponding α, α-dichloro compound with hydrogen fluoride in the presence of a catalytic amount of an antimony(V) compound (EP-A 168 344). This reaction is also carried out in the liquid phase.

This process has the disadvantage that it cannot be used for certain substrates (see Comparative Examples 1+2) and that it cannot be carried out continuously.

A process has now been found for preparing perfluoroalkoxy(alkylthio)-benzenes of the formula (I)

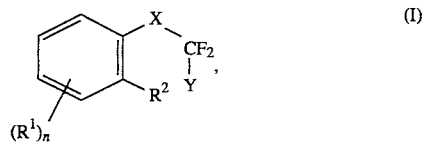

in which
R$^1$ represents fluorine, chlorine, bromine, C$_1$–C$_4$ -fluoroalkyl, COF, COCl, C$_1$–C$_4$-alkyl, C$_1$–C$_4$-alkoxy or C$_1$–C$_4$-fluoroalkoxy, R$^2$ represents hydrogen, C$_1$–C$_4$-fluoroalkyl, fluorine, chlorine or bromine and Y represents C$_1$–C$_4$-fluoroalkyl or R$^2$ and Y together represent an oxygen or sulphur atom or an —OCHal$_2$— or —SCHal$_2$— group, with R$^2$ then marking the position of the O or S atom and Hal$_2$ in each case being Cl$_2$, FCl or F$_2$, n represents zero, 1 or 2 and X represents oxygen or sulphur, which is characterized in that a perfluorochloroalkoxy(alkylthio)-benzene of the formula (II)

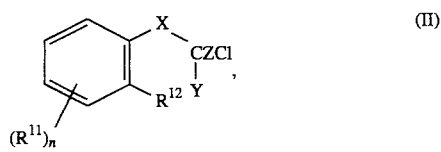

in which
X, Y and n have the meaning given above and
R$^{11}$ represents fluorine, chlorine, bromine, C$_1$–C$_4$-halogeneoalkyl, COF, COCl, C$_1$–C$_4$-alkyl, C$_1$–C$_4$-alkoxy or C$_1$–C$_4$-halogenoalkoxy, R$^{12}$ represents hydrogen, C$_1$–C$_4$-halogenoalkyl, fluorine, chlorine or bromine or R$^{12}$ and Y together have the meaning given above for R$^2$ and Y together and Z represents fluorine or chlorine,
is reacted with hydrogen fluoride in the gas phase and in the presence of a catalyst.

The starting materials for the process of the invention, namely perfluorochloroalkoxy(alkylthio)-benzenes of the formula (II), are known compounds (see, for example, EP-A 168 344, DE-A 3 329 126 and DE-A 3 409 438) or can be obtained in an analogous way to known compounds.

If use is made of compounds of the formula (II) in which R$^{11}$ represents halogenoalkyl or halogenoalkoxy and/or R$^{12}$ represents halogenoalkyl and at least one of these contains at least one halogen atom which is not fluorine, then those halogen atoms which are not fluorine are replaced by fluorine atoms in the process of the invention.

The process of the invention preferably uses perfluorochloroalkoxy-benzenes of the formula (II) in which R$^{11}$ represents fluorine, chlorine, C$_1$–C$_2$-halogenoalkyl or C$_1$–C$_2$-alkoxy, R$^{12}$ represents hydrogen, Y represents trifluoromethyl or R$^{12}$ and Y together represent an oxygen atom or an OCF$_2$—, OCCl$_2$— or OCFCl— group, X represents oxygen and n represents zero or 1 and preferably gives the corresponding perfluoroalkoxybenzenes of the formula (I). The process of the invention particularly preferably uses 2,2,3,3-tetrachlorobenzodioxane, 2,2-dichloro-3,3-difluorobenzodioxane, 2-chloro-2,3,3-trifluorobenzodioxane, 4-(1,1-dichloro2,2,2-trifluoroethoxy) -chlorobenzene or 4-(1,1-dichloro2,2,2-trifluoroethylthio)methylbenzene and gives 2,2,3,3-tetrafluorobenzodioxane, 4-(perfluoroethoxy)chlorobenzene or 4-(perfluoroethylthio)-methylbenzene.

The process of the invention is carried out in the gas phase. This means that the perfluorochloroalkoxy(alkylthio)-benzenes of the formula (II) are passed together with hydrogen fluoride in gaseous form over a catalyst which is, for example, fixed or in a fluidized bed. Optionally, an inert gas can also be added. The reaction temperature can be, for example, in the range from 200° to 500° C., preferably from 250° to 450° C. The pressure is selected, for example in the range from 0.5 to 3 bar, in such a way that the abovementioned reactants are in the gas phase. Frequently, at appropriately high reaction temperatures, it is possible to operate at atmospheric pressure.

The hydrogen fluoride used may be the commercial anhydrous grade.

Suitable catalysts are catalysts customarily used for halogen exchange reactions in the gas phase. For example, the following can be used: halides and oxides of metals and transition metals. Suitable catalysts are, in particular, chlorides, fluorides and/or optionally mixed oxides of copper, chromium, iron, bismuth, zinc, lanthanum, cerium, zirconium, vanadium, molybdenum, tungsten and/or nickel. Preference is given to tungsten and/or nickel. Preference is given to chromium(III) salts alone or in admixture with chlorides of the other specified metals and/or fluorides thereof and/or oxides thereof. The catalysts can be used as such, for example in particulate form, but also applied to a support material, for example aluminium oxide, magnesium oxide, magnesium fluoride, calcium fluoride, zinc chloride and/or graphite.

In general it is advantageous to pre-treat the catalyst with hydrogen fluoride and subsequently with elemental chlorine prior to being exposed to a compound of the formula (II).

The amount in which catalysts are used in the process of the invention is not critical. For economic considerations, the amount of catalyst is advantageously selected such that a conversion of at least 70% is achieved. For example, from 50 g to 5 kg per hour of the perfluorochloroalkoxy(alkylthio)-benzene of the formula (II) can be passed over one litre of catalyst.

Hydrogen fluoride can, for example, be used in amounts from 0.5 to 10 mol, based on one equivalent of chlorine to be replaced. Preferably, from 1 to 8 mol of hydrogen fluoride are used, based on one equivalent of chlorine to be replaced.

The reaction mixture obtained after passing over the catalyst can, after cooling and condensation, be worked up, for example, by removing any hydrogen fluoride still present, for example by phase separation or by distillation, and fractionally distilling the residue or pouring the residue freed of hydrogen fluoride onto ice, and separating off the organic phase formed and fractionally distilling it.

The process of the invention gives perfluoroalkoxy(alkylthio)-benzenes of the formula (I) in high yields and purities with long catalyst lifetimes. It can also be advantageously used for those starting materials which hardly react at all in the desired manner in the liquid phase (see Comparative Examples 1+2).

In view of the prior art indicated in the introduction, this was completely surprising.

EXAMPLES

Comparative Example 1

50 g of 2-chloro-2,3,3-trifluorobenzodioxane and 25 g of antimony trifluoride were heated to 180° C. After 2 hours boiling under reflux, 2 ml of antimony pentachloride were added and the mixture was maintained for a further 3 hours at 150° C. After cooling to room temperature, the reaction mixture was poured onto a mixture of 200 ml of water and 50 ml of concentrated hydrochloric acid, the organic phase was separated off and distilled. 8 g of 2,2,3,3-tetrafluorobenzodioxane and 22 g of unchanged starting material were obtained.

Comparative Example 2

500 ml of hydrogen fluoride, 5 ml of antimony pentachloride and 150 g of 2-chloro-2,3,3-trifluorobenzodioxane were heated in a closed vessel for 6 hours at 40° C., excess hydrogen fluoride was then drawn off, and the residue was taken up in methylene chloride, rendered alkaline and stem-distilled. The re-distillation gave 27 g of 2,2,3,3-tetrafluorobenzodioxane having a boiling point from 142° to 146° C. at 1020 mbar.

Comparative Example 3

In a nickel tube which was electrically heatable from the outside and had an internal diameter of 30 mm, 350 ml of aluminium oxide (SPH 501) were activated with hydrogen fluoride and 150 ml/hour of hydrogen fluoride (measured as liquid) and 148 g/hour of 2-chloro-2,3,3-trifluorobenzodioxane were passed over the catalyst at 315° C. After 2 hours, a sample was taken from the gaseous reaction mixture and analyzed by gas chromatography. The sample contained only 3% by weight of 2,3,3-tetrafluoro-1,3-benzodioxane.

Example 1 of the invention 600 g of $Cr(NO_3)_3 \cdot 9H_2O$ were dissolved in 300 ml of water. 420 g of magnesium oxide and 420 g of graphite were added to this solution and the resulting paste-like mass was compounded. The paste-like product obtained therefrom was cut up into cubes having an edge length of 0.5 cm and then dried for 16 hours at 100° C.

350 ml of the catalyst thus prepared were introduced into the nickel tube also used in Comparative Example 3 and 5 mol of hydrogen fluoride were then passed through at 350° C. over a period of 3 hours. The hydrogen fluoride was used in admixture with nitrogen (molar ratio 1:2). Subsequently, 35 g/h of chlorine gas were passed through for 4 hours.

Finally, 170 ml/h of hydrogen fluoride (measured as liquid) and 148 g/h of 2-chloro-2,3,3-trifluorobenzodioxane were passed over the catalyst at 300° C. In the course of 7 hours, 930 g of 2,2,3,3-tetrafluorobenzodioxane were obtained. This corresponds to a degree of fluorination of 97%.

Example 2 of the invention 500 g of a particulate alumina (SPH 501) support material were impregnated with 125 g of $CrCl_3 \cdot 6H_2O$ dissolved in 800 ml of water, subsequently dried, treated with a 25% by weight strength ammonia solution, then washed free of salts and dried.

400 ml of the catalyst thus prepared were introduced into the nickel tube also used in Comparative Example 3 and subsequently 5 mol of hydrogen fluoride were passed through at 350° C. over a period of 3 hours. A mixture of hydrogen fluoride and nitrogen in a molar ratio of 1:2 was used. 35 g/h of chlorine gas were then passed through for 4 hours.

Subsequently, 140 ml/h of hydrogen fluoride (measured as liquid) and 110 g/h of 2-chloro-2,3,3-trifluorobenzodioxane were passed over the catalyst at 300° C. In the course of 6 hours, 600 g of 2,2,3,3-tetrafluorobenzodioxane were obtained. This corresponds to a yield of 98%.

Example 3 of the invention

The procedure was as in Example 2 of the invention, but 110 ml/h of hydrogen fluoride (measured as liquid) and 100 g/h of 4-(1,1-dichloro-2,2,2-trifluoroethoxy)chlorobenzene were passed over the catalyst at 300° C. In the course of 2 hours, 165 g of 4-(perfluoroethoxy)chlorobenzene were obtained. This corresponds to a yield of 93.5%.

Example 4 of the invention

The procedure was as in Example 2, but 110 ml/h of hydrogen fluoride and 28 g/h of 4-(1,1-dichloro-2,2,2-trifluoroethylthio)-methylbenzene were passed over the catalyst at 300° C. In the course of 2 hours, 47.3 g of 4-(perfluoroethylthio)-methylbenzene were obtained. This corresponds to a yield of 95%.

$^1H$ and $^{19}F$-NMR data of 4-(perfluoroethylthio)-methylbenzene: $^1H$-NMR δ=2.38 (s, 3H), 7.2 (d, 2H), 7.55 (d,2H); $^{19}F$-NMR δ=−83 (t, 3F), −92.67 (q, 2F).

What is claimed is:

1. A process for preparing perfluoroalkoxy(alkylthio)-benzenes of the formula (I),

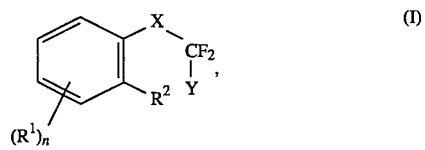

in which $R^1$ represents fluorine, chlorine, bromine, $C_1$–$C_4$-fluoroalkyl, COF, $C_1$–$C_4$-alkyl, $C_1$–$C_4$-alkoxy or $C_1$–$C_4$-fluoroalkoxy, $R^2$ represents hydrogen, $C_1$–$C_4$-fluoroalkyl, fluorine, chlorine or bromine and Y represents $C_1$–$C_4$-fluoroalkyl or $R^2$ and Y together represent an oxygen or sulphur atom or an —OCHal$_2$— or —SCHal$_2$-group, with $R^2$ then marking the position of the O or S atom and Hal$_2$ in each case being Cl$_2$, FCl or F$_2$, n represents zero, 1 or 2 and X represents oxygen or sulphur, which process comprises that a perfluorochloroalkoxy(alkylthio)benzene of the formula (II)

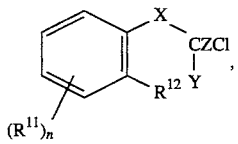

(II)

in which

X, Y and n have the meaning given above and $R^{11}$ represents fluorine, chlorine, bromine, $C_1$–$C_4$-halogenoalkyl, COF, COCl, $C_1$–$C_4$-alkyl, $C_1$–$C_4$-alkoxy or $C_1$–$C_4$-halogenoalkoxy, $R^{12}$ represents hydrogen, $C_1$–$C_4$-halogenoalkyl, fluorine, chlorine or bromine or $R^{12}$ and Y together have the meaning given above for $R^2$ and Y together and Z represents fluorine or chlorine, is reacted with hydrogen fluoride in the gas phase and in the presence of a catalyst selected from the group consisting of chlorides, fluorides and oxides of copper, chromium, iron, bismuth, zinc, lanthanum, cerium, zirconium, vanadium, molybdenum, tungsten, nickel, and combinations thereof.

2. The process of claim 1, in which the perfluorochloroalkoxy-benzenes of the formula (II) which are used are ones in which $R^{11}$ represents fluorine, chlorine, $C_1$–$C_2$-halogenoalkyl or $C_1$–$C_2$-alkoxy, $R^{12}$ represents hydrogen, Y represents trifluoromethyl or $R^{12}$ and Y together represent an oxygen atom or an OCF$_2$—, OCCl$_2$— or OCFCl— group, X represents oxygen and n represents zero or 1.

3. The process of claim 1, which is carried out at temperatures in the range from 200° to 500° C. and at such pressures in the range from 0.5 to 3 bar that the reactants are in the gas phase.

4. The process of claim 1, wherein said catalyst is applied to a support material.

5. The process of claim 4, wherein said support material is a support material selected from the group consisting of aluminum oxide, magnesium oxide, magnesium fluoride, calcium fluoride, zinc chloride, graphite and combinations thereof.

6. The process of claim 1, in which said catalysts are chromium(III) salts.

7. The process of claim 1, in which from 50 g to 5 kg per hour of the perfluorochloroalkoxy(alkylthio)-benzene of the formula (II) are passed over said catalyst.

8. The process of claim 1, in which hydrogen fluoride is used in amounts from 0.5 to 10 mol, based on one equivalent of chlorine to be replaced.

* * * * *